United States Patent
Scarpellini et al.

(10) Patent No.: US 9,890,356 B2
(45) Date of Patent: Feb. 13, 2018

(54) USE OF G-CSF IN IN VITRO EMBRYO CULTURE

(71) Applicants: Fabio Scarpellini, Rome (IT); Marco Sbracia, Rome (IT)

(72) Inventors: Fabio Scarpellini, Rome (IT); Marco Sbracia, Rome (IT)

( * ) Notice: Subject to any disclaimer, the term of this patent is extended or adjusted under 35 U.S.C. 154(b) by 0 days.

(21) Appl. No.: 14/429,191

(22) PCT Filed: Sep. 17, 2013

(86) PCT No.: PCT/EP2013/002798
§ 371 (c)(1),
(2) Date: Mar. 18, 2015

(87) PCT Pub. No.: WO2014/044382
PCT Pub. Date: Mar. 27, 2014

(65) Prior Publication Data
US 2015/0225694 A1    Aug. 13, 2015

(30) Foreign Application Priority Data

Sep. 19, 2012    (IT) .............................. MI2012A1562

(51) Int. Cl.
C12N 15/00    (2006.01)
C12N 5/00    (2006.01)
C12N 5/073    (2010.01)

(52) U.S. Cl.
CPC ........ *C12N 5/0604* (2013.01); *C12N 2501/22* (2013.01)

(58) Field of Classification Search
CPC ........................... C12N 5/0604; C12N 2501/22
USPC ....................................................... 435/325
See application file for complete search history.

(56) References Cited

FOREIGN PATENT DOCUMENTS

WO    WO 2013113658 A1 *    8/2013    ........... C12N 5/0037

OTHER PUBLICATIONS

Devroey (2004, Human Reproduction Update, 10:19-28).*
Ledee (2008, Human Reproduction, 23 :2001-2009).*
Thouas (Oct. 2012; Fertility and Sterility, S167, Abstract #P191).*
Nelissen (May 2012, Human Reprod, 27:1966-1976).*
Naib, et al., "Regulation of non-classical major histocompatibility complex class I mRNA expression in bovine embryos,", Journal of Reproductive Immunology SEP 2011, vol. 91, No. 1-2, Sep. 2011 pp. 31-40.
Takahashi et al., "In vitro development of bovine one-cell embryos: Influence of glucose,lactate, pyruvate, amino acids and vitamins.", Theriogenology, May 1992, vol. 37 No. 5, pp. 963-978.
Sjoblom et al., "Granulocyte-macrophage colony-stimulating factor promotes human blastocyst development in vitro.", Human Reproduction, Dec. 1999, vol. 14 No. 12, pp. 3069-3076.
Scarpellini, et al., "Use of granulocyte colony-stimulating factor for the treatment of unexplained recurrent miscarriage: a randomised controlled trial.", Human Reproduction, Nov. 2009, vol. 24 No. 11, pp. 2703-2708.
Richter, K., "The importance of growth factors for preimplantation embryo development and in-vitro culture.", Current Opinion in Obstetrics & Gynecology, Jun. 2008, vol. 20, No. 3, pp. 292-304.
Gandhi et al., "A single medium supports development of bovine embryos throughout maturation, fertilization and culture.", Human Reproduction Feb. 2000, vol. 15, No. 2, pp. 395-401.
International Search Report of PCT/EP2013/002798, dated Jan. 3, 2014.

* cited by examiner

*Primary Examiner* — Valarie E Bertoglio
(74) *Attorney, Agent, or Firm* — Silvia Salvadori, P.C.; Silvia Salvadori

(57) ABSTRACT

An in vitro culture medium for embryos consisting of IVF culture medium additionally containing G-CSF at a concentration of at least 0.5 ng/ml, preferably between 1.0 and 5.0 ng/ml, is described; a method for in vitro embryo culture, comprising the steps of incubating a plurality of embryos in an in vitro culture medium consisting of IVF culture medium additionally containing G-CSF at a concentration of at least 0.5 ng/ml and growing such embryos until the 8-cell stage is reached is also described.

7 Claims, 2 Drawing Sheets

USE OF G-CSF IN IN VITRO EMBRYO CULTURE

This application is a U.S. national stage of PCT/EP2013/002798 filed on 17 Sep. 2013, which claims priority to and the benefit of Italian Application No. MI2912A001562, filed on 19 Sep. 2012, the contents of which are incorporated herein by reference in their entireties.

FIELD OF APPLICATION

This invention relates to the use of granulocyte colony stimulating factor (G-CSF) in the in vitro culture of embryos, in particular human embryos.

PRIOR ART

G-CSF is a glycoprotein of molecular weight 19.6 kilodaltons comprising 174-180 amino acids, the gene for which is located on chromosome 17 at locus q11.2q12. Its specific membrane receptor in cells is G-CSF-R or CD 114, present on neutrophils, myeloid cells and stem cells. G-CSF is secreted by immunocompetent cells, embryo cells and placental cells, as well as by stem cells.

Its role, initially considered to be fundamentally that of activating the production of neutrophils, is that of promoting the activation, growth and differentiation of stem cells and other types of undifferentiated cells.

Its therapeutic use was initially restricted to the treatment of post-chemotherapy neutropenia in cancer patients, but it has subsequently been extended to all patients treated with stem cell transplants to promote their growth and engraftment, to patients with myocardial infarction treated with stem cells to promote cardiac revascularization, to patients with spinal cord lesions to promote post-traumatic recovery and to patients with Alzheimer's disease.

In the field of human reproduction it has been observed that G-CSF is produced in the trophoblast, which also expresses its specific receptor since the very first stages of pregnancy. It has also been observed that G-CSF is present in ovarian follicles and regulates oocyte maturation and follicle rupture at the time of ovulation. G-CSF is also produced by the embryo during its very first stages (4-8 cell stage); its presence is considered to be an indication of good oocyte competence and embryo well-being, as pointed out by various authors.

In a work by the Applicants in 2009 (Human Reproduction, Vol. 24, N. 11, pp. 2703-2708, 2009), it was demonstrated that in women suffering from Recurrent Miscarriage, the therapeutic use of G-CSF made it possible to take pregnancies to term in a significantly higher percentage in comparison with controls. Also the administration of G-CSF to women undergoing in vitro fertilization increased the possibility of pregnancy, as demonstrated by other authors.

It is also known that one of the stages in the procedure of in vitro fertilization which follows follicular aspiration of the oocytes obtained following ovarian stimulation and their fertilization with spermatozoa, possibly through the ICSI technique, is that of the in vitro culture of fertilized oocytes or embryos until the 8-cell stage is reached and they are finally transferred to the uterus.

This stage of in vitro culture is performed using artificial culture media, which may remain unchanged throughout the entire culture period or which may be sequentially varied. These culture media typically contain glucose, pyruvate and components capable of providing energy, but amino acids, nucleotides, vitamins and cholesterol may also be added to improve embryo growth and development.

A typical culture medium for embryos is IVF™ medium, produced and sold by the Swedish firm Vitrolife, which contains a bicarbonate buffer, glucose, lactate, pyruvate, human serum albumin and EDTA. This medium was first marketed as "IVF-50", in that it was sold as 50 ml bottles and is presently marketed as "IVF-30" (30 ml bottles).

The use of culture media with added GM-CSF ("Granulocyte-macrophage colony stimulating factor") to promote the development of human embryos in vitro has been proposed (C. Sjöblom et al., "Granulocyte-macrophage colony-stimulating factor promotes human blastocyst development in vitro", Human Reproduction vol. 14, no. 12, pp 3069-3076, 1999).

A culture medium for human embryos from in vitro fertilization, known as Embryogen®, containing GM-CSF, has also been subsequently marketed.

A significant increase in the number of embryos implanted in women with a history of recurrent miscarriage has been achieved through the use of this culture medium.

Al Naib et al., "Regulation of non-classical major hystocompatibility complex class I mRNA expression in bovine embryos", Journal of Reproductive Immunology, vol. 91, no. 1-2, September 2011, pp. 31-40, disclose the in vitro culture of bovine embryos in synthetic oviduct fluid (SOF) medium supplemented with various growth factors and cytokines including G-CSF at concentrations of 0.1, 1, 10 and 100 ng/ml until the blastocyst stage. In this article it is reported that G-CSF has no effect on bovine embryo development in vitro.

The problem underlying the present invention is that of providing a culture medium for embryos in vitro which makes it possible to obtain a greater percentage of implanted embryos in comparison with that obtained using known culture media.

SUMMARY OF THE INVENTION

The abovementioned problem has been resolved by providing an in vitro culture medium for embryos consisting of IVF culture medium additionally containing G-CSF at a concentration of at least 0.5 ng/ml.

In the present application the term "embryos" relates to fertilized mammalian oocytes, in particular fertilized human oocytes.

Preferably the concentration of G-CSF is comprised between 1.0 and 5.0 ng/ml, advantageously it is about 2 ng/ml.

By IVF culture medium it is meant the IVF™ medium, produced and sold by the Swedish firm Vitrolife, mentioned before.

This culture medium comprises a physiologically acceptable bicarbonate buffer capable of maintaining the pH in the range of 7.4 to 7.6.

This culture medium further comprises glucose, lactate, pyruvate, human serum albumin and EDTA.

In a further aspect this invention relates to a method for in vitro culture of embryos comprising the steps of:

incubating a plurality of embryos in an in vitro culture medium consisting of IVF culture medium additionally containing G-CSF at a concentration of at least 0.5 ng/ml and growing the embryos until the 8-cell stage is reached.

Preferably the abovementioned culture medium contains between 1.0 and 5.0 ng/ml, advantageously 2 ng/ml, of G-CSF.

Preferably the abovementioned embryos are obtained through in vitro fertilization of oocytes by ICSI (intracytoplasmic sperm injection).

DETAILED DESCRIPTION

Further characteristic features and advantages of the present invention will become apparent from the examples provided hereinbelow by way of illustration and without limitation.

Example 1

The efficacy of G-CSF in promoting embryo growth and development was evaluated in a series of experiments performed on 30 female mice superovulated with mare's serum gonadotropin and then caused to ovulate with chorionic gonadotropin and fertilized by male mice. These female mice were sacrificed the day after appearance of the vaginal plug, a sign that fertilization had occurred, and the embryos were recovered from the oviducts by flushing at the two-cell stage. The embryos from each mouse were divided into two equivalent groups to obtain two groups of embryos obtained from the same animals, in such a way that one acted as a control for the other. One group of embryos (totaling 170 embryos) was incubated with a culture medium (HTF) to which G-CSF (Granulokyne) was added in a final concentration of 1 ng/ml in microdrops of 10 microliters each under mineral oil (paraffin), with three embryos per microdrop. The other group of embryos (totaling 173 embryos), used as a control, was incubated in HTF alone in microdrops of 10 microliters under mineral oil with three embryos per microdrop.

The embryos were checked every day until they reached the blastocyst stage (5 days incubation) and, where applicable, until their hatching and adhesion to the plastic of the Petri dish.

Figure 1:
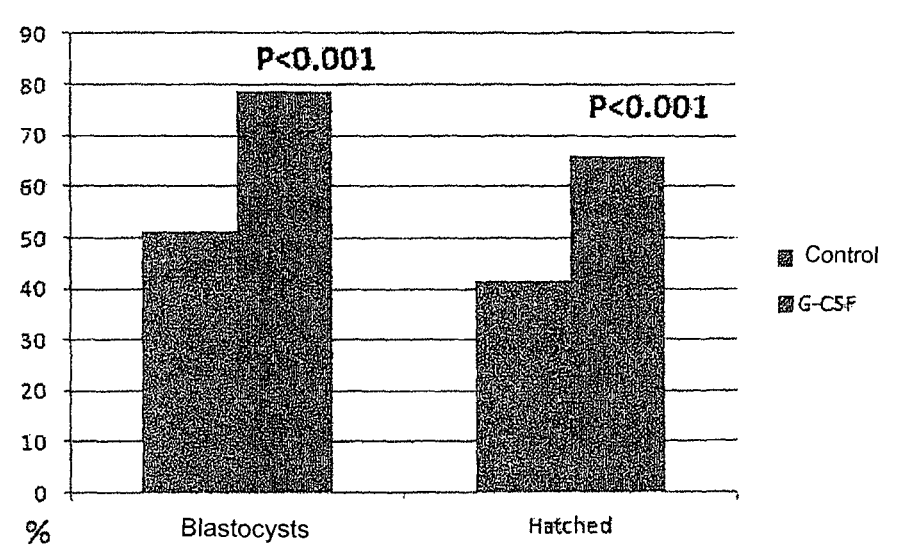
FIG. 1 is a diagrammatic illustration of the results of the experiments according to Example 1 described below.

Analysis of the observations on embryos revealed (see FIG. 1) that the use of G-CSF for embryo culture enabled 133 embryos out of 170 to reach the blastocyst stage and 119 out of 170 to hatch, while in the control only 89 of 173 embryos became blastocysts and 72 of these hatched ($P<0.001$).

Example 2

The efficacy of G-CSF in promoting embryo growth and development at different concentrations, i.e. 0.1 ng/ml, 0.5 ng/ml, 1 ng/ml, 2 ng/ml and 5 ng/ml respectively, was evaluated in a series of experiments performed on 30 female mice superovulated with mare's serum gonadotropin and then caused to ovulate with chorionic gonadotropin and fertilized by male mice. These female mice were sacrificed the day after appearance of the vaginal plug, a sign that fertilization had occurred, and the embryos were recovered from the oviducts by flushing at the two-cell stage. The embryos from each mouse were divided into six equivalent groups to obtain as many groups of embryos obtained from the same animals, in such a way that one acted as a control for the other. One group of embryos (totaling 70 embryos) was incubated with a culture medium (HTF) to which G-CSF (Granulokyne) was added in a final concentration of 0.1 ng/ml in microdrops of 10 microliters each under mineral oil (paraffin), with three embryos per microdrop. One group of embryos (totaling 76 embryos) was incubated with a culture medium (HTF) to which G-CSF (Granulokyne) was added in a final concentration of 0.5 ng/ml in microdrops of 10 microliters each under mineral oil (paraffin), with three embryos per microdrop. One group of embryos (totaling 75 embryos) was incubated with a culture medium (HTF) to which G-CSF (Granulokyne) was added in a final concentration of 1 ng/ml in microdrops of 10 microliters each under mineral oil (paraffin), with three embryos per microdrop. One group of embryos (totaling 78 embryos) was incubated with a culture medium (HTF) to which G-CSF (Granulokyne) was added in a final concentration of 2 ng/ml in microdrops of 10 microliters each under mineral oil (paraffin), with three embryos per microdrop. One group of embryos (totaling 77 embryos) was incubated with a culture medium (HTF) to which G-CSF (Granulokyne) was added in a final concentration of 5 ng/ml in microdrops of 10 microliters each under mineral oil (paraffin), with three embryos per microdrop.

Another group of embryos (totaling 73 embryos), used as a control, was incubated in HTF alone in microdrops of 10 microliters under mineral oil with three embryos per microdrop.

The embryos were checked every day until they reached the blastocyst stage (5 days incubation) and, where applicable, to their hatching and adhesion to the plastic of the Petri dish.

Figure 2:
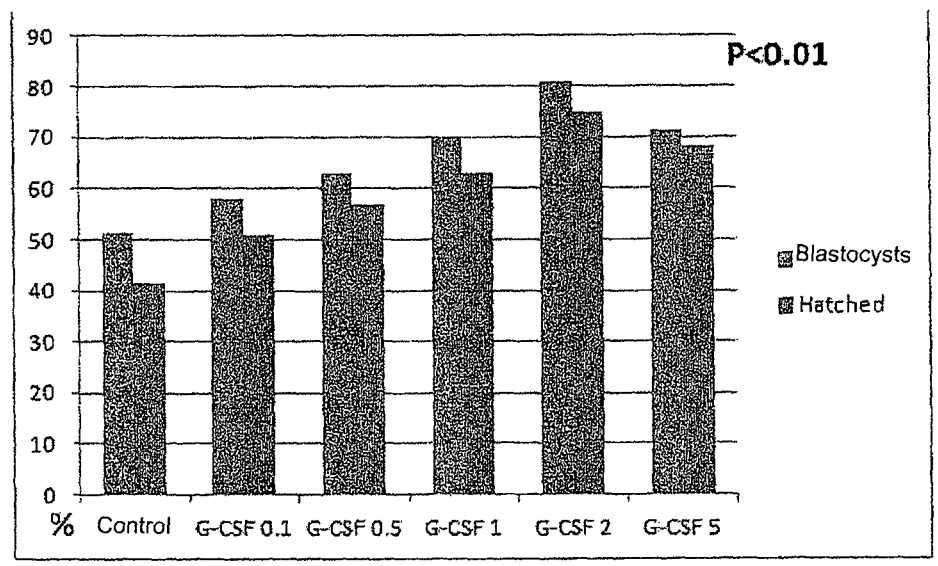
FIG. 2 is a diagrammatic illustration of the results of the experiments according to Example 2 described below.

Analysis of the observations on the embryos showed (see FIG. 2) that the use of G-CSF for embryo culture in a concentration of 2 ng/ml brought about optimum growth ($P<0.001$).

Example 3

In a series of experiments performed on 20 female mice superovulated with mare's serum gonadotropin and then caused to ovulate with chorionic gonadotropin the oocytes were collected and fertilized in vitro with mouse semen by IVF to evaluate the role of G-CSF in promoting growth of the embryos obtained in vitro. These female mice were sacrificed the day after the chorionic gonadotropin was administered, and the oocytes were recovered from the oviducts by flushing. These were then fertilized with 100,000 mouse spermatozoa in microdrops of 5 microliters. On the next day the occurrence of fertilization was evaluated by observing whether pronuclei were present. The embryos of each mouse obtained in this way were divided into two equivalent groups so as to obtain two groups of embryos obtained from the same animals, in such a way that one acted as a control for the other. One group of embryos (totaling 98 embryos) was incubated with a culture medium (HTF) to which G-CSF (Granulokyne) was added in a final concentration of 2 ng/ml in microdrops of 10 microliters each under mineral oil (paraffin) with three embryos per microdrop. The other group of embryos (totaling 101 embryos), used as a control, was incubated in HTF alone in microdrops of 10 microliters under mineral oil with three embryos per microdrop.

The embryos were checked every day until they reached the blastocyst stage (5 days incubation) and, where applicable, until their hatching and adhesion to the plastic of the Petri dish.

Figure 3:
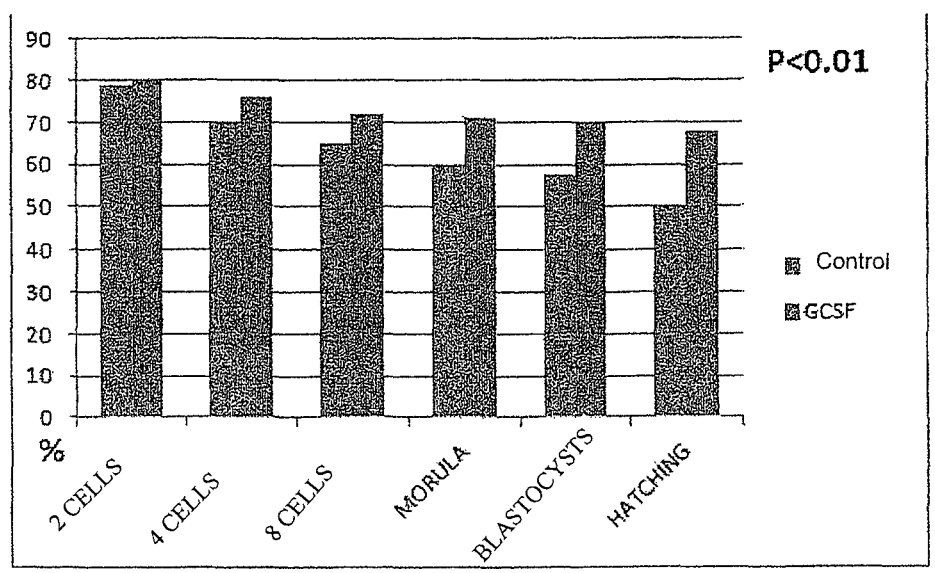
FIG. 3 is a diagrammatic illustration of the results of the experiments according to Example 3 described below.

Analysis of the observations on the embryos revealed (see FIG. 3) that the use of G-CSF for embryo culture brought about a greater yield in terms of embryos reaching the blastocyst and hatching stage (P<0.001).

Example 4

In this experiment the role of adding G-CSF up to a final concentration of 2 ng/ml in the culture medium for human embryos obtained by in vitro fertilization through ICSI was evaluated. 20 patients with repeated failures in previous attempts at in vitro fertilization (at least three) aged under 38 years were selected and subdivided into two groups of 10 each. After standard ovarian stimulation in the two groups through the administration of 0.1 mg of Decapeptyl every day from the 21st day of the previous cycle to the day on which HCG was administered and of 225 IU of Gonal-f from the first day of the cycle until an optimum ovarian response was obtained, oocyte maturation was induced with 10,000 IU of HCG. The oocytes were collected after 36 hours by echo-guided transvaginal follicular aspiration. The oocytes recovered in this way were treated with hyaluronidase to remove the cumulus oophorus and were fertilized by ICSI as described in the literature (Palermo G, Joris H, Devroey P, Van Steirteghem A C. "Pregnancies after intracytoplasmic injection of single spermatozoon into an oocyte", Lancet 1992; 340:17-8.). 18 hours after ICSI the occurrence of fertilization was evaluated by observing whether any pronuclei were present. At this point, in the study group (10 patients) the fertilized oocytes were incubated in IVF-50 medium (produced by Vitrolife AB) supplemented with G-CSF (Granulokyne) in a concentration of 2 ng/ml, while in the control group (10 cases) the oocytes were incubated in IVF-50 alone.

On the third day it was evaluated how many embryos had reached the 8-cell stage and 3 embryos per patient were transferred into the uterus in both the groups. The number of class A embryos obtained on the third day, the number of pregnancies achieved and the number of implanted embryos were evaluated as the main results.

The results shown in Table 1 below reveal that medium supplemented with G-CSF brought about a significant increase in the number of pregnancies, implanted embryos and class A embryos obtained in comparison with the control.

TABLE 1

|  | Medium with G-CSF | Control | P |
| --- | --- | --- | --- |
| No. of patients | 10 | 10 |  |
| No. of oocytes treated | 77 | 79 |  |
| Fertilized | 69 | 70 |  |
| Class A embryos | 51 | 41 | 0.0413 |
| Pregnancies | 7 | 3 | 0.086 |
| Implanted embryos | 11/30 | 3/30 | 0.0152 |

Example 5

In this experiment the culture medium according to the invention containing G-CSF in a final concentration of 2 ng/ml was compared with a new recently marketed medium containing GM-CSF, another growth factor acting on stem cells, in the culture of human embryos obtained by in vitro fertilization using ICSI.

20 patients with repeated failures in previous attempts at in vitro fertilization (at least three) aged under 38 years were selected and subdivided into two groups of 10 each. After standard ovarian stimulation in the two groups through the administration of 0.1 mg of Decapeptyl every day from the 21st day of the previous cycle to the day on which HCG was administered and of 225 IU of Gonal-f from the first day of the cycle until an optimum ovarian response was obtained, oocyte maturation was induced with 10,000 IU of HCG. The oocytes were collected after 36 hours by echo-guided transvaginal follicular aspiration. The oocytes recovered in this way were treated with hyaluronidase to remove the cumulus oophorus and were fertilized by ICSI as described in the literature (Palermo G, Joris H, Devroey P, Van Steirteghem A C. "Pregnancies after intracytoplasmic injection of single spermatozoon into an oocyte", Lancet 1992; 340:17-8.). 18 hours after ICSI the occurrence of fertilization was evaluated by observing whether any pronuclei were present. At this point, in the study group (10 patients) the fertilized oocytes were incubated in IVF-50 medium supplemented with G-CSF (Granulokyne) in a concentration of 2 ng/ml, while in the control group (10 cases) the oocytes were incubated in Embryogen® medium produced by the company Origio (Denmark), containing GM-CSF.

On the third day it was evaluated how many embryos had reached the 8-cell stage and 3 embryos per patient were transferred into the uterus in both the groups. The number of class A embryos obtained on the third day, the number of pregnancies achieved and the number of implanted embryos were evaluated as the main results.

The results shown in Table 2 below reveal that medium supplemented with G-CSF brought about a significant increase in the number of pregnancies, implanted embryos and class A embryos obtained in comparison with the medium containing GM-CSF (Embryogen®).

TABLE 2

|  | Medium with G-CSF | Embryogen ® | P |
| --- | --- | --- | --- |
| No. of patients | 10 | 10 |  |
| No. of oocytes treated | 72 | 71 |  |
| Fertilized | 66 | 65 |  |
| Class A embryos | 52 | 40 | 0.0242 |
| Pregnancies | 8 | 4 | 0.0849 |
| Implanted embryos | 12/30 | 4/30 | 0.0195 |

It is therefore apparent that the culture medium according to this invention constitutes a significant improvement in comparison with the culture medium which has hitherto provided the best performance in embryo culture, that is the Embryogen® medium.

The invention claimed is:

1. An in vitro culture medium for human embryos consisting of culture medium containing bicarbonate buffer, glucose lactate, pyruvate, human serum albumin and EDTA and additionally containing G-CSF at a concentration of at least 0.5 ng/ml.

2. The culture medium according to claim 1, wherein the concentration of G-CSF is comprised between 1.0 and 5.0 ng/ml.

3. The culture medium according to claim 1, wherein the concentration of G-CSF is about 2 ng/ml.

4. A method for in vitro culture of human embryos comprising the steps of:

incubating a plurality of embryos in an in vitro culture medium consisting of culture medium containing bicarbonate buffer, glucose lactate, pyruvate, human serum albumin and EDTA and additionally containing G-CSF at a concentration of at least 0.5 ng/ml, and
growing said embryos until the 8-cell stage is reached.

5. The method according to claim 4, wherein said culture medium contains 1.0 to 5.0 ng/ml of G-CSF.

6. The method according to claim 4, wherein said culture medium contains about 2 ng/ml of G-CSF.

7. The method according to claim 4, wherein said human embryos are obtained through in vitro fertilization of oocytes by ICSI (intracytoplasmic sperm injection).

* * * * *